United States Patent [19]

Utahara

[11] Patent Number: 4,471,886

[45] Date of Patent: Sep. 18, 1984

[54] DEVICE FOR SPRAYING MEDICINAL LIQUID

[76] Inventor: Sadaji Utahara, 78, Ikomadai-minami, Ikoma Nara Prefecture, Japan

[21] Appl. No.: 473,562

[22] Filed: Mar. 9, 1983

[30] Foreign Application Priority Data

Apr. 6, 1982 [JP] Japan .................................. 57-57860

[51] Int. Cl.³ .......................... B67D 5/22; B65D 83/14
[52] U.S. Cl. ................................. 222/48; 222/402.17; 222/443; 141/20; 251/353
[58] Field of Search ............................. 222/41, 46–48, 222/394, 402.1, 402.16, 402.17, 402.18, 402.2, 222/402.24, 443, 476, 477, 519, 520, 526, 537; 141/18, 20, 21, 98; 251/350, 353, 354

[56] References Cited

U.S. PATENT DOCUMENTS

| | | | |
|---|---|---|---|
| 3,081,916 | 3/1963 | Rhodes et al. | 141/20 X |
| 3,173,585 | 3/1965 | Kahn | 141/20 X |
| 3,180,536 | 4/1965 | Meshberg | 222/443 X |
| 3,225,969 | 12/1965 | O'Donnell | 222/402.18 |
| 3,278,093 | 10/1966 | Lehmann | 222/402.17 |

FOREIGN PATENT DOCUMENTS 1287126 8/1972 United Kingdom ........... 222/402.16

Primary Examiner—Joseph J. Rolla
Assistant Examiner—Michael S. Huppert
Attorney, Agent, or Firm—Mason, Fenwick & Lawrence

[57] ABSTRACT

A spray device comprising a bomb, a measuring container housed in the bomb, and a plunger valve adapted to discharge a medicinal liquid and having a valve cutout at its lower end. The plunger has a medicinal liquid replenishing port formed in a radial direction at a portion thereof other than the cutout portion, communicating with a channel in the plunger and usually covered with a sleeve portion of the measuring container. When the bomb is empty or is emptied of the liquid, a new medicinal solution or replenishment is charged into the bomb from outside through the plunger. The peripheral side surface of a neck portion of the plunger and the top outer surface of the bomb close to the surface are formed with marks for setting the valve in position for replenishment.

7 Claims, 8 Drawing Figures

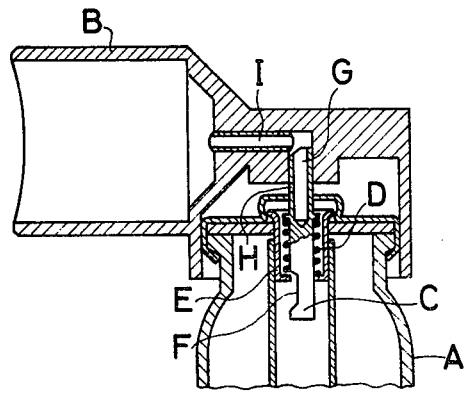
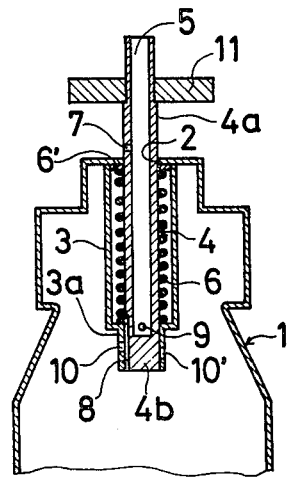
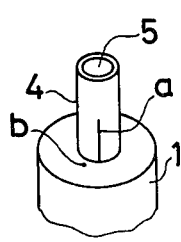
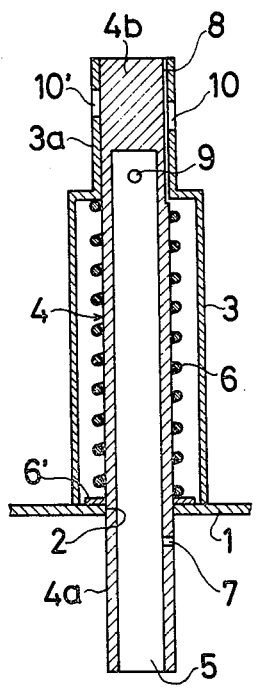
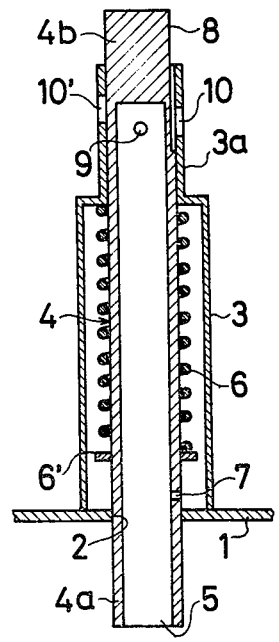

DEVICE FOR SPRAYING MEDICINAL LIQUID

BACKGROUND OF THE INVENTION

The medicinal liquid to be sprayed, for example, to the bronchus for treating an attack of asthma is available as contained in a small-sized hand spray container for the patient himself to apply the liquid in an event of an attack. However, the device is of such a construction that it is not reusable when the medicinal preparation contained in the small container has been consumed.

FIG. 1 shows the construction of the device, which will be used in the following manner. When a spray adaptor B is mounted on the head of a medicinal liquid bomb A and is then depressed, a plunger C is slightly pushed into the bomb A against the action of a spring D. Whereas the interior of the bomb A has been in communication with the interior of a measuring container E around the plunger C through a lower recessed portion F of the plunger C, the recessed portion F is pushed out from the lower end of the container E by the above movement to bring the container E out of communication with the interior of the bomb A. The plunger C, projecting upward from the upper end of the measuring container E, has a hollow channel G and a hole H. Simultaneously with the above movement, the portion of the plunger C having the hole H in communication with the channel G is forced into the container E. Consequently a specified quantity of medicinal liquid measured out and accommodated in the container E around the plunger C is forced through the hole H and the channel G and discharged from the adaptor B through a passageway I therein. Even if the adaptor B is held depressed continuously, no more liquid will be discharged other than the measured-out quantity. When the adaptor B is returned, another portion of the medicinal liquid is measured out in preparation for the next application.

With devices of such known construction, the medicinal liquid can be sprayed in specified quantities by measuring-out spray means such as the one described above, but after the medicinal liquid contained in the bomb A has been wholly discharged, it is impossible to replenish the bomb A with the medicinal liquid. Accordingly the assembly of the spray adaptor and the bomb incorporating measuring-out spray means is used only for a limited amount of liquid and is discarded after the liquid has been consumed. Thus the device is costly and uneconomical in view of savings in resources.

Spray devices of the type described are available as filled with a specific medicinal preparation of a pharmaceutical company. However, if it is possible for the pharmaceutist or hospital to fill such a device with a medicinal preparation in accordance with the symptoms of a particular patient, the device would be appropriate and beneficial to both the pharmaceutist or doctor and the patient.

The prior art already described is disclosed, for example, in U.S. Pat. Nos. 3,818,908 and 3,900,138. Nevertheless we have found no prior art as to a device which comprises a disposable bomb incorporating a measuring-out spray means and a spray adaptor and which is made replenishable with a medicinal liquid for reuse.

Further we have been unable to discover any prior-art device which is conveniently usable for spraying a medicinal liquid either in specified quantities or continuously in an unlimited quantity, selectively, as contemplated by the present invention.

SUMMARY OF THE INVENTION

An object of the present invention is to overcome the uneconomical aspect of the conventional spray device and to provide a novel device for spraying a medicinal liquid which can be replenished with the medicinal liquid with great ease for repeated use.

Another object of the invention is to provide a spray device which is repeatedly replenishable with the desired liquid medicinal preparation by the patient and which is therefore continuously usable without being disposed of.

Another object of the invention is to provide a device for spraying a medicinal liquid in which a bomb having measuring-out means incorporated therein is adapted to discharge the liquid in two modes, i.e., in specified constant quantities and continuously in an indefinite quantity so as to achieve an enhanced therapeutic effect by the application of the medicinal liquid.

Other features of the present invention will become apparent from the following detailed description of embodiments given with reference to the accompanying drawings.

BRIEF DESCRIPTION OF THE DRAWINGS

FIG. 1 is a view in vertical section showing a conventional device;

FIG. 2 is a view in vertical section showing an embodiment of the invention;

FIG. 3 is a fragmentary perspective view of the same;

FIG. 4 and FIG. 5 are fragmentary enlarged views in section showing the embodiment as inverted from the position shown in FIG. 2 and as set for spraying in constant quantities, FIG. 4 showing a plunger before pushing and FIG. 5 showing the same after pushing;

DESCRIPTION OF THE PREFERRED EMBODIMENTS

Figure 6:
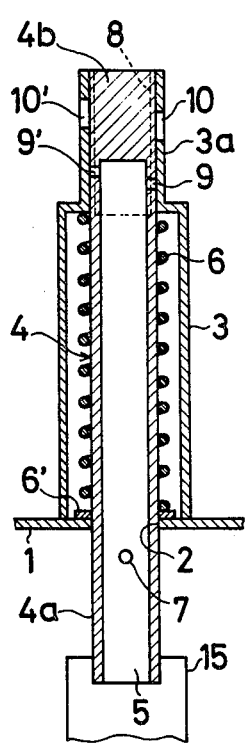
FIG. 6 and FIG. 7 are fragmentary enlarged views in section showing the embodiment as set for liquid replenishment or continuous spraying, FIG. 6 showing the plunger before pushing and FIG. 7 showing the same after pushing.

The present invention will be described below with reference to an embodiment which is a device for spraying a medicinal solution for treating attacks of asthma. With reference to FIG. 2 et seq., a medicinal solution bomb 1 is internally provided with a measuring container 3 under the top opening 2 thereof. A plunger 4 having a channel 5 is inserted in the container 3. A spring 6 housed in the measuring container 3 and bearing against a flange 6' fixed to the plunger 4 biases the plunger 4 upward so that a neck portion 4a of the plunger is usually positioned outside the bomb 1. The neck portion 4a has a small communication hole 7 which communicates with the interior of the measuring container 3 when the plunger 4 is pushed into the container 3 against the spring 6. The plunger 4 is formed at its lower end 4b with a vertical cutout portion 8 through which the interior of the container 3 usually communicates with the outside thereof and which blocks the communication when the plunger 4 is depressed. The plunger 4 further has a medicinal solution replenishing port 9 formed at a portion thereof other than the cutout portion 8 and located at a position different from that of the hole 7 about the axis of the plunger 4. The port 9 is in communication with the lower end of the channel 5 and is so positioned that it is usually covered with a container sleeve portion 3a fitting around the plunger 4.

The sleeve portion 3a of the measuring container 3 has a communication aperture 10 which directly or indirectly communicates with the interior of the bomb 1 and which is opposed to the replenishing port 9 when the plunger 4 is rotated to a solution replenishing position and depressed against the spring 6.

With the measuring container 3 and the plunger 4 thus constructed, the communication between the interior of the container 3 and the interior of the bomb 1 through the cutout portion 8 is blocked by the depression of the plunger 4 as described above, and the communication hole 7 is shifted to the interior of the measuring container 3. While the replenishing port 9 is so positioned that it will not communicate with the communication aperture 10 when the plunger 4 of the plunger valve is pushed, only a specified quantity of medicinal solution confined in the measuring container 3 around the plunger 4 is forced out from the channel 5 via the hole 7. However, if the port 9 is in the replenishing position in communication with the aperture 10 when the plunger 4 is pushed, the solution in the bomb 1 is supplied to the channel 5, with the result that the solution is jetted out continuously while the plunger 4 is pushed.

Figure 7:
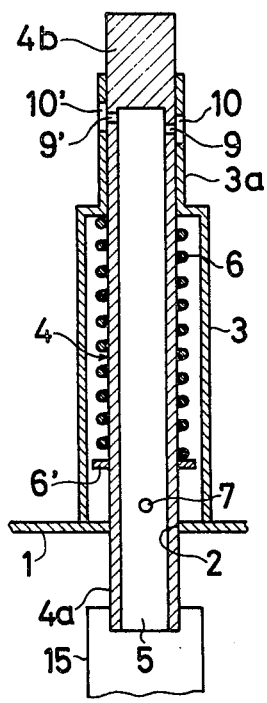

The plunger 4 is rotated to the replenishing position when the bomb 1 is to be replenished with an amount of medicinal solution after the solution within the bomb 1 has been consumed. Stated more specifically with reference to FIG. 7 wherein the device is shown as turned upside down, a medicinal replenishing container 15 is fitted to the outer end of the plunger 4 and pushed toward the bomb 1, and the outlet of the container 15 is opened. When the port 9 of the plunger 4 is brought into communication with the aperture 10 of the measuring container 3, the solution is forced out from the container 15 into the bomb 1 through the communicating portion. At this time, the container 3 is also filled with a portion of the solution through the hole 7.

To assure efficient replenishment, a second replenishing port 9' and a second communication aperture 10' may be formed in addition to the port 9 and the aperture 10 as slightly displaced from the port 9 and the aperture 10 axially of the plunger 4, with the port 9' positioned at an angle of 180° with the port 9 about the axis of the plunger 4.

If in this case the cutout portion 8 and the communication hole 7 are formed in the plunger 4 on the same side, with the replenishing port 9 formed at a right angle with the hole 7 about the axis, the cutout portion 8 can be positioned most away from the communication apertures 10 and 10' during replenishment. This eliminates the occurrence of leakage or like trouble during replenishment.

It is convenient to make the replenishing position of the plunger 4 relative to the bomb 1 coincide with the position in which a line mark a formed on the peripheral side surface of the plunger 4 projecting from the top opening 2 of the bomb 1 is set to a spot mark b provided on the top outer surface of the bomb 1 close to the peripheral surface as shown in FIG. 3.

The ports 9, 9' can be properly brought into communication with the apertures 10. 10' in the replenishing position by a stopper 11 (FIG. 2) attached to a portion of the plunger 4 outside the bomb 1 and adapted to come into contact with the outer surface of the bomb 1 exactly at the position where the ports are in communication with the corresponding apertures. However, the communication apertures 10 and 10' may each be in the form of a slit extending axially of the plunger 4 to increase the range of communication between each port and the corresponding aperture. In this case, the ports 9, 9' can be brought into communication with the apertures 10, 10' easily without the stopper 11.

Figure 8:
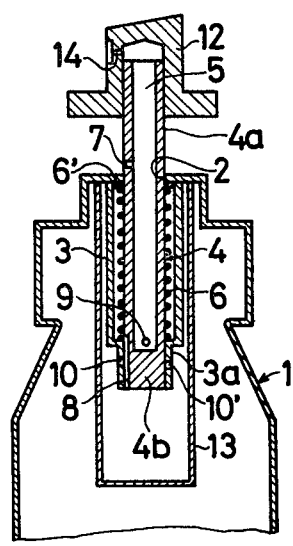
FIG. 8 is a sectional view showing another embodiment of the invention.

FIG. 8 shows another embodiment, in which a plunger manipulating member 12 is fitted to the outer end of a plunger 4. A bomb 1 has a discharge container 13 housing a measuring container 3. In this case, a medicinal solution can be sprayed from an orifice 14 formed in the manipulating member 12 upon the depression of the member 12. The bomb 1 may be replenished with the solution in the same manner as above, with the manipulating member 12 removed from the plunder 4.

The device of the present invention is not only adapted to spray a medicinal liquid in constant quantities or continuously but is also replenishable with a supply of liquid, so that the device is repeatedly usable for savings in the required expenditure and economical use of resources.

The medicinal liquid is of course contained in the bomb of the invention along with a harmless liquefied gas.

What is claimed is:

1. A device for spraying a medicinal liquid comprising a mcdicinal liquid bomb, a measuring container provided within the bomb at the top portion thereof, and a plunger having a channel and rotatably fitting in the measuring container, the plunger being so biased as to cause a neck portion thereof to be projected outward from the bomb, the plunger neck portion being formed with a small communication hole usually positioned outside the bomb but communicating with the interior of the measuring container when the plunger is pushed, the plunger having an inner end formed with a cutout portion for usually causing the interior of the measuring container to communicate with the outside thereof but blocking the communication when pushed, the plunger having a medicinal liquid replenishing port formed at a portion of the inner end thereof other than the cutout portion and located at a position different from that of the hole about the axis of the plunger, the replenishing port being in communication with the channel and being usually covered with a sleeve portion of the measuring container fitting around the plunger, the measuring container being formed with a communication aperture adapted to communicate with the replenishing port when the plunger is rotated to a medicinal liquid replenishing position and pushed.

2. A device as defined in claim 1 wherein the peripheral side surface of the plunger projecting from the top opening of the bomb and the top outer surface of the bomb close to the peripheral side surface are each formed with a positioning mark for medicinal liquid replenishment.

3. A device as defined in claim 1 wherein the cutout portion and the communication hole are formed in the plunger on the same side thereof, and the replenishing port is positioned at a right angle with the communication hole about the axis of the plunger.

4. A device as defined in any one of claims 1 which has two medicinal liquid replenishing ports and two communication apertures.

5. A device as defined in any one of claims 1 wherein a portion of the plunger projecting from the bomb is provided with a stopper for positioning the replenishing port in communication with the corresponding communication aperture.

6. A device as defined in any one of claims 1 wherein the communication aperture is in the form of a slit extending axially of the plunger.

7. A device as defined in claim 6 wherein a plunger manipulating member formed with a discharge orifice is fitted to the outer end of the plunger.

* * * * *